United States Patent
DiMarzio et al.

(10) Patent No.: US 7,193,215 B2
(45) Date of Patent: Mar. 20, 2007

(54) SYSTEM AND METHOD FOR IMAGING OF COATED SUBSTRATES

(75) Inventors: Don DiMarzio, Northport, NY (US); Robert Silberstein, New York, NY (US); John Weir, Huntington, NY (US)

(73) Assignee: Northrop Grumman Corporation, Los Angeles, CA (US)

(*) Notice: Subject to any disclaimer, the term of this patent is extended or adjusted under 35 U.S.C. 154(b) by 0 days.

(21) Appl. No.: 11/211,304

(22) Filed: Aug. 25, 2005

(65) Prior Publication Data

US 2007/0012877 A1 Jan. 18, 2007

Related U.S. Application Data

(63) Continuation of application No. 10/213,599, filed on Aug. 6, 2002, now abandoned.

(51) Int. Cl.
*G01N 21/35* (2006.01)
(52) U.S. Cl. .................. 250/341.8; 250/339.11
(58) Field of Classification Search ............. 250/341.8, 250/339.03, 358.1
See application file for complete search history.

(56) References Cited

U.S. PATENT DOCUMENTS

| | | | |
|---|---|---|---|
| 4,484,081 A | 11/1984 | Cornyn, Jr. et al. | |
| 4,647,220 A | 3/1987 | Adams et al. | |
| 4,682,222 A | 7/1987 | Smith et al. | |
| 4,878,116 A | 10/1989 | Thomas et al. | |
| 4,988,875 A | 1/1991 | Ortiz et al. | |
| 5,065,630 A | 11/1991 | Hadcock et al. | |
| 5,266,806 A | 11/1993 | Barber | |
| 5,287,183 A | 2/1994 | Thomas et al. | |
| 5,582,485 A | 12/1996 | Lesniak | |
| 5,703,362 A | 12/1997 | Devitt et al. | |
| 5,714,758 A | 2/1998 | Neu | |
| 5,763,786 A | 6/1998 | Chaplin et al. | |
| 5,963,653 A | 10/1999 | McNary et al. | |
| 6,000,844 A | 12/1999 | Cramer et al. | |
| 6,184,528 B1 | 2/2001 | DiMarzio et al. | |
| 6,489,992 B2 | 12/2002 | Savoye | |
| 6,495,833 B1 | 12/2002 | Alfano et al. | |
| 6,515,285 B1 | 2/2003 | Marshall et al. | |
| 6,597,448 B1 | 7/2003 | Nishiyama et al. | |
| 6,784,428 B2 * | 8/2004 | Rabolt et al. ........... 250/339.02 |
| 6,795,175 B2 * | 9/2004 | Hunt ........................ 356/237.2 |
| 6,943,353 B2 * | 9/2005 | Elmore et al. ......... 250/339.02 |

FOREIGN PATENT DOCUMENTS

WO   WO 0120319 A1   3/2001

* cited by examiner

*Primary Examiner*—Otilia Gabor
(74) *Attorney, Agent, or Firm*—Stetina Brunda Garred & Brucker (57) ABSTRACT

The present invention relates to a system for imaging the surface of a substrate through a coating on the substrate. The system includes an infrared light source positioned to cast an infrared light upon the substrate to thereby create reflected light. A focal plane array may be positioned to receive the reflected light and generate an image therefrom. At least one optical filter may be disposed between the substrate and the focal plane array so as to pass only coating transparent wavelengths of the reflected light along an optical path between the infrared light source and the focal plane array thereby visually revealing irregular structural features of the substrate as at least one image.

31 Claims, 4 Drawing Sheets
(2 of 4 Drawing Sheet(s) Filed in Color)

Fig. 1

Corrosion Under Paint

Fig. 2A — Visible Image, Unpainted Aluminum

Fig. 2B — IR Image, *Painted* Aluminum

SYSTEM AND METHOD FOR IMAGING OF COATED SUBSTRATES

CROSS-REFERENCE TO RELATED APPLICATIONS

The application is a continuation of U.S. patent application Ser. No. 10/213,599, filed Aug. 6, 2002 now abandoned.

STATEMENT RE: FEDERALLY SPONSORED RESEARCH/DEVELOPMENT

The U.S. Government has a paid-up license in this invention and the right in limited circumstances to require the patent owner to license to others on reasonable terms as provided for by the terms of Contract No. DACA 72-99-C-0011 awarded by SERDP.

BACKGROUND

The present invention relates generally to analysis of substrates which are coated, and more particularly to a system and method for imaging the surface of a substrate which is coated through the coating for the purposes of detecting rust, pitting, corrosion, cracks, scratches, gouges, and other structural imperfections.

Aircraft components are subject to constant degradation caused by environmental conditions. Various agents including moisture, dust, wind, solar radiation, and air pollutants cause damage to components in the form of rust or corrosion. Although the application of a coating, such as paint, reduces these problems substantially, it typically cannot eliminate them entirely. Moreover, other causes such as stress experienced during flight can result in damage which a coating of paint cannot mitigate, such as stress defects and cracking. While the occurrence of these forms of damage is to be expected, the particular rate at which any given aircraft's components degrade is highly dependent upon the particular environment of the aircraft and the circumstances under which it operates. This is readily apparent at aircraft maintenance depots, where maintenance personnel sometimes have the opportunity to view two aircraft of similar make and age. In many instances, the need for repair or replacement of components is much greater for one such aircraft than for the other. It is therefore impractical to rely upon projected maintenance schedules in determining when an aircraft will need repair. The only effective way to ensure that aircraft are ready for flight is through periodic inspection.

Using traditional methods, inspection of aircraft components is accomplished by means of visual inspection. When visually inspecting aircraft components, the coating used to protect the components becomes an obstacle because it may hide structural defects beneath. It is therefore necessary to strip the component assembly or aircraft in question of its paint before a proper inspection can be performed. Afterward, a new coating of paint must be applied. Obviously, this process results in substantial expense in the form of labor and materials, and likewise requires a great amount of time. It has been estimated that an aircraft spends twelve percent of its life in some form of maintenance or inspection, and billions of dollars are spent on aircraft maintenance every year. Apart from the inefficiency of visual inspection methods, another problem is the fact that visual inspection is simply not as effective as might be desired. While a skillful eye may pick up most human-visible defects with a satisfactory degree of consistency, some defects may be very small or lie under the surface of the component. In many cases these defects will go unnoticed by the naked human eye, regardless of the skill and experience of the observer. It is therefore desirable to devise a method for analyzing damage to aircraft components without the need to strip paint from the component or rely upon the human eye alone. Some inventions offer insight into how this problem might be solved.

One such invention is described in U.S. Pat. No. 5,426,506 entitled OPTICAL METHOD AND APPARATUS FOR DETECTION OF SURFACE AND NEAR-SUBSURFACE DEFECTS IN DENSE CERAMICS issued to Ellingson, et al. The invention described therein employs a laser of a wavelength calculated to penetrate the surface of an object to be analyzed. The laser is passed through a polarizer before being reflected by the object, and through a second polarizer afterward. When striking the object, that portion of light which strikes irregularities is reflected at an altered polarity, while the portion which strikes regular features is reflected at its original polarity. The second polarizer is configured to detect this difference, and the system generates an image reflecting it. In order to generate an image of an area, the object to be analyzed is secured to a mount capable of translation and/or rotation and controlled by a computer or similar device. The object is moved about under the laser beam, to thereby be scanned. The most obvious disadvantage of this system is that in order to perform area analysis, a motorized mount typically must be used. This appears to preclude the possibility of a hand-held unit, and the system would be highly impractical when applied to components or assemblies already mounted on aircraft. Another obvious disadvantage is the method is not used to see surfaces under organic coatings and the wavelength of the laser light will not penetrate coatings or polymers.

A second related invention is disclosed in U.S. Pat. No. 4,682,222 entitled STIMULATED SCANNING INFRA-RED SYSTEM issued to Smith et al. The invention uses a collimated energy beam, such as a laser, to heat an object to be analyzed. Because objects radiate infrared light when they are warm, an infrared detector can then be used to detect the heat of areas of the object relative to each other. For instance, because areas which are cracked will heat at a different rate than other areas, they can thereby be distinguished. The obvious disadvantage of this system is that the object to be scanned must be heated. For various reasons, methods involving heating the object to be analyzed are not ideal. For instance, a thermal shielding component of an aircraft with a coating of paint would pose a particular problem for this system. The component is specifically designed to be difficult to heat, and any source powerful enough to heat the component would likely damage the coating of paint. This patent additionally utilizes a technique of thermography which does not relate to IR imaging of substrate surfaces under organic coatings.

Still another related invention is disclosed in U.S. Pat. No. 6,184,528 entitled METHOD OF SPECTRAL NONDE-STRUCTIVE EVALUATION issued to DiMarzio, et al. The invention disclosed therein employs an infrared light source, such as an infrared laser, to cast infrared light upon a substrate. Reflected light is measured as a function of wavelength to obtain reflectivity data. The reflectivity data of the sample substrate is compared to reflectivity data of a control substrate. Correlations are then drawn between differences in order to determine the presence of corrosion. This invention achieves some of the objectives of the present invention, but will not detect the full range of structural features detectable by the present invention and does not provide a visual image of the substrate.

It is therefore desirable to devise a system and method for analyzing substrates free of the aforementioned drawbacks and, further, improving upon previous systems in terms of effectiveness and resolution.

BRIEF SUMMARY OF THE INVENTION

In accordance with the present invention, there is provided a system for imaging the surface of a substrate through a coating on the substrate. Coatings typically found on substrates are designed to be opaque in the visible range of the spectrum, and are often more transparent in the infrared area of the spectrum. An infrared light source may be positioned to cast infrared light upon the substrate to thereby create reflected light. A focal plane array may be positioned so as to receive the reflected light and generate an image therefrom. At least one spectral optical filter may be disposed between the substrate and the focal plane array so as to pass only coating transparent wavelengths of the reflected light along an optical path between the infrared light source and the focal plane array thereby visually revealing structural features of the substrate as at least one image. A multiplicity of optical filters disposed between the substrate and the focal plane array may be employed which are operative to generate images in a plurality of selected wavelengths for imaging structural features of the substrate. A multiple imaging device may be placed into communication with the focal plane array for simultaneously imaging a plurality of structural features of the substrate.

Further, a computer may be employed which is combining and enhancing images generated by the system to thereby generate collective images of selected structural features of the substrate. A computer programmed with substrate patterns for color-coding selected structural features of the substrate within the image based on the substrate patterns may be provided so as to provide visual categorization of the structural features. Additionally, a position sensor may be employed to mark reference points on the surface of the substrate so as to store coordinates of structural features of the substrate. A computer formed to compare images generated at selected wavelengths in a feedback loop may be provided so as to automatically enhance image quality of irregular selected structural features of the substrate based upon preselected enhancement criteria. Advantageously, the infrared light source, the focal plane array and the at least one optical filter may be collectively formed with a handheld device so as to be transportable by as single human operator.

The system may also include a first polarizer disposed between the infrared light source and the substrate for polarizing the infrared light to a first selected polarity. Additionally, a second polarizer may be disposed between the substrate and the focal plane array for polarizing the reflected light to a second selected polarity. The first selected polarity and the second selected polarity may be oppositely configured so as to prevent reflected light corresponding to regular features of the substrate from being received upon the focal plane array. The polarities of the first and second polarizers may be rotatable so as to selectably provide a plurality of polarities for imaging irregular structural features from the substrate.

In use, there is also provided a method for imaging the surface of a substrate through a coating on the substrate. The method includes directing infrared light upon the substrate. The infrared light may be reflected from the substrate to thereby create reflected light. Only coating transparent wavelengths of the reflected light may be filtered. The reflected light may be received on a focal plane array and an image may be generated from the focal plane array so as to visually reveal irregular structural features of the substrate.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

DETAILED DESCRIPTION

Figure 1:
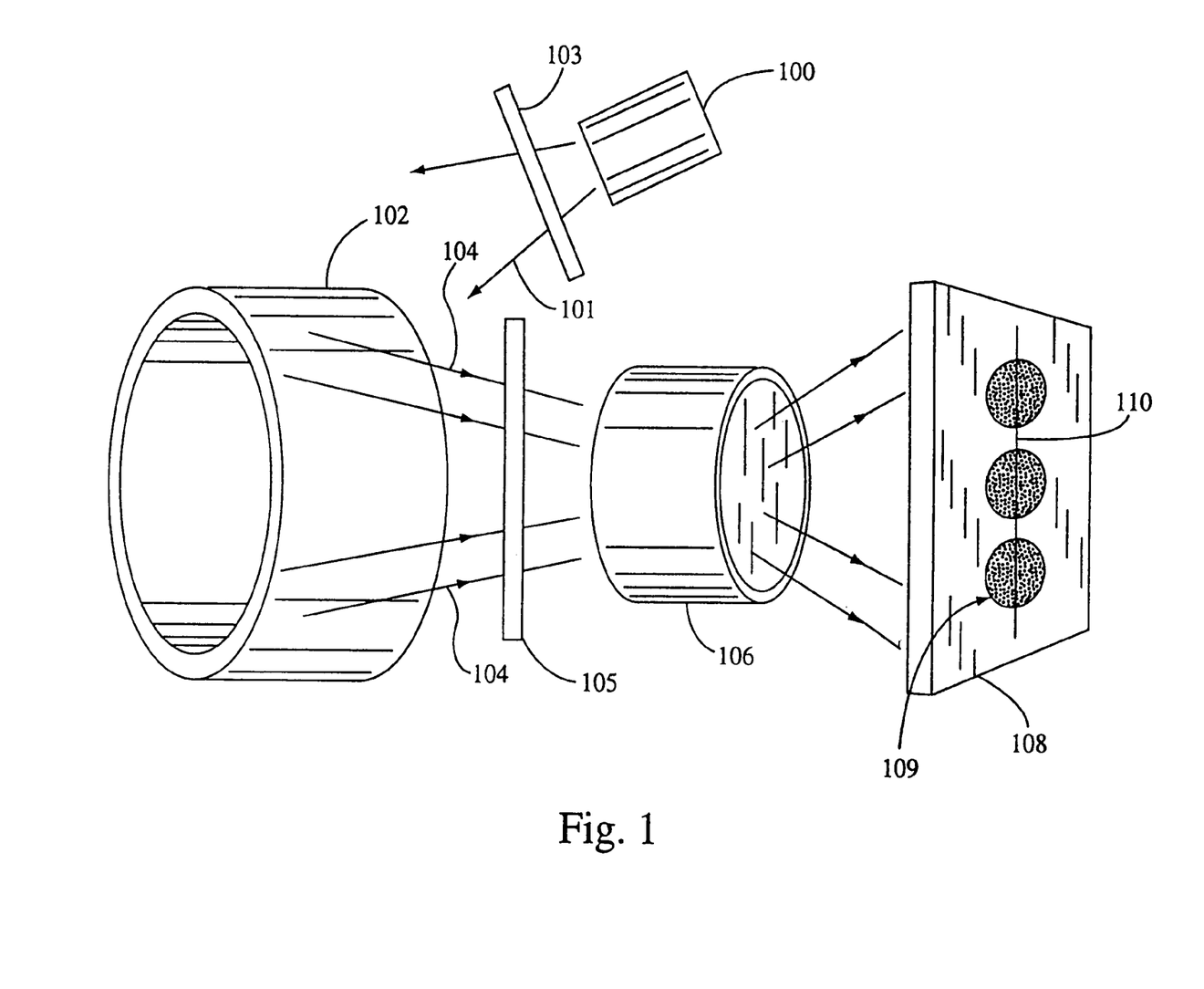
FIG. 1 illustrates an embodiment of the system and method of the present inventions

Referring now to the drawings wherein the showings are for purposes of illustrating embodiments of the present invention only, and not for purposes of limiting the same, FIG. 1 illustrates an embodiment of the system and method of the present invention. An infrared light source 100 is used to cast infrared light 101 in the direction of a substrate 102 which is coated. In an embodiment of the invention, prior to reaching the substrate 102, the infrared light 101 may pass through a first polarizer 103. The first polarizer 103 is operative to polarize the infrared light to a first selected polarity.

Light reflected by the substrate creates reflected light 104. In an embodiment, the reflected light 104 passes through a second polarizer 105. The second polarizer 105 is operative to polarize the reflected light to a second selected polarity. For instance, the second polarizer 105 may be configured to polarize the reflected light 104 in a direction opposite to that of first selected direction, a method known as "cross-polarity." In this case, light of the polarity modulated by the first polarizer 103 will not pass through the second polarizer 105. According to basic principles of optics, the portion of the reflected light 104 which was reflected off of regular areas of the substrate 102 will retain the polarity modulated by the first polarizer 103 and therefore will not pass through the second polarizer 105. However, the portion of the reflected light 104 which was reflected off of irregular areas, such as corrosion or rust, will have an altered polarity and will therefore pass through the second polarizer 105. Additionally, this polarization technique can reduce scattering by pigments in the coating which results in a clearer image of the substrate. Thus, only the portion of the reflected light 104 which was reflected off of irregular areas of the substrate 102 will pass through the second polarizer 105. The first polarizer 103 and second polarizer 105 may therefore operate in tandem to highlight the areas of the substrate 102 which are irregular because they are corroded or otherwise damaged. Additionally, the polarity modulated by the first polarizer 103 may be configured to allow viewing of the substrate 102 at various levels. This is because light of a polarity parallel to the substrate 102 will more easily reflect off of the coating, while light of a polarity perpendicular to the substrate 102 will more easily penetrate through the coating to the substrate beneath. Accordingly, it is possible to focus on either the surface of the substrate itself or on the surface of the coating. Of course, this methodology may be combined with the cross-polarity method described above in order to enhance particular features of the substrate at a particular level. It should be noted that although the first polarizer 103 and second polarizer 105 may be used in the fashion described and are therefore present in a potentially preferred embodiment, they are not necessary to the function of the present invention, and need not be included.

Subsequent to passing through the second polarizer 105 (if present), the reflected light 104 passes through an optical filter 106. The optical filter 106 is operative to filter out all except selected wavelengths of the reflected light 104. Coatings used on, for instance, aircraft components and assemblies are generally designed to be opaque in the visible range of light. Often, they are more transparent in the infrared range of light. Accordingly, certain wavelengths of light are more likely to pass through the coating to be reflected by the substrate beneath. The image created by the portion of the reflected light 104 having these wavelengths will represent an image primarily of the substrate 102 instead of the coating on the substrate. It is therefore desirable to focus on these wavelengths to the exclusion of others, and they become the selected wavelengths passed by the optical filter 106. The optical filter 106 need not be a single filter, but could be a series of filters.

Subsequent to passing through the second polarizer 105 (if present) and optical filter 106, the reflected light 104 reaches a focal plane 108. A focal plane array (not shown) is positioned at a focal plane 108 for the purpose of receiving an image 109 created by the reflected light 104 at the focal plane 108. Structural features of the substrate 102, such as cracks 110 are visible in this image 109. The focal plane array is operative to take this image 109 and generate it as a photograph, image on an LCD display, or otherwise represent it on a human-viewable medium.

Figure 2A:
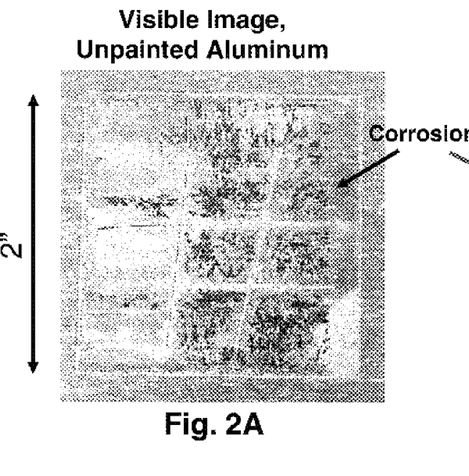
FIG. 2A is a visible image of an unpainted selectively corroded aluminum substrate on a chemical film treated (Ref. Mil-c-5541) aluminum coupon.
Figure 2B:
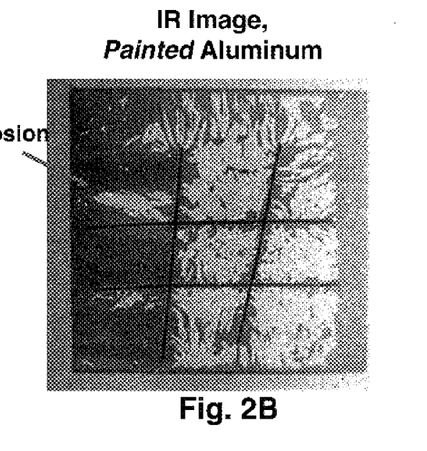
FIG. 2B is an IR image of the same aluminum coupon as shown in FIG. 2A. However, in this case the substrate or aluminum coupon has been tested with 0.006" (6 mils) of primer and top coat. The corrosiveness was made visible under the coating by means of the system and method of the present invention.
Figure 3:
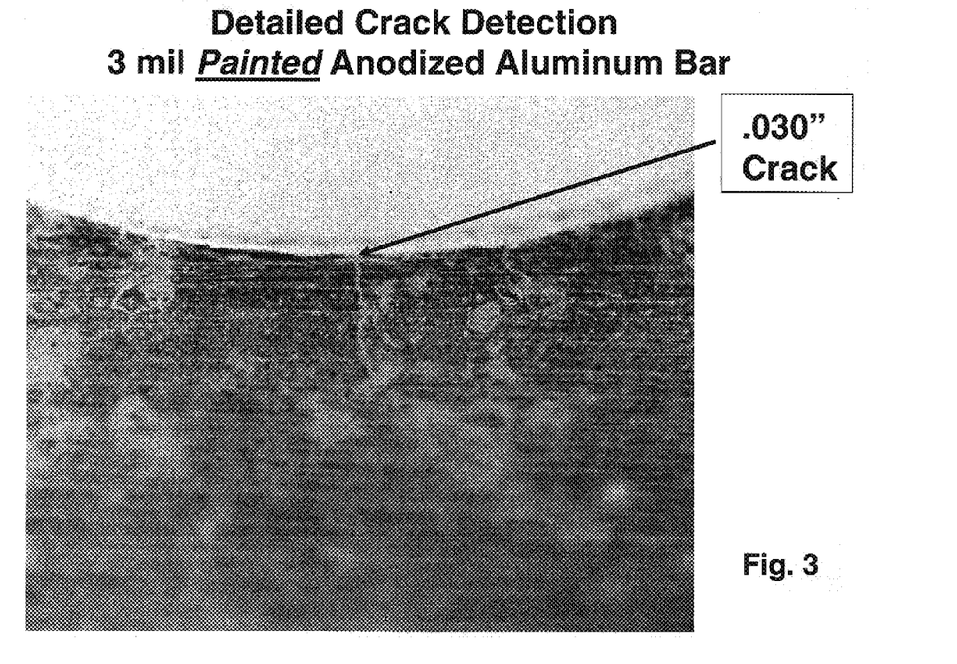
FIG. 3 is an IR Image taken of a fatigue crack on a hole radius and made visible under a coating by means of the system and method of the present invention.

FIGS. 2A, 2B, and 3 demonstrate the effectiveness of the system and method of the present invention. FIG. 2A is a visible image of an unpainted substrate, in this case a chemical film treated (Ref mil-c-5541) aluminum coupon. The structural features of the substrate are visible to the human eye. FIG. 2B is an image of the same Alodined aluminum coupon. However, in this case the substrate has been coated with a 0.006" thickness (6 mils) of primer and a top coat. The structural features of the substrate are only visible because this image was generated using the system and method of the present invention. FIG. 3 is an image of a fastener hole, with a crack in it made visible by means of the system and method of the present invention. Experiments proved detectability of cracks as small as 0.030" in length and pits as small as 0.001" in diameter.

Figure 4:
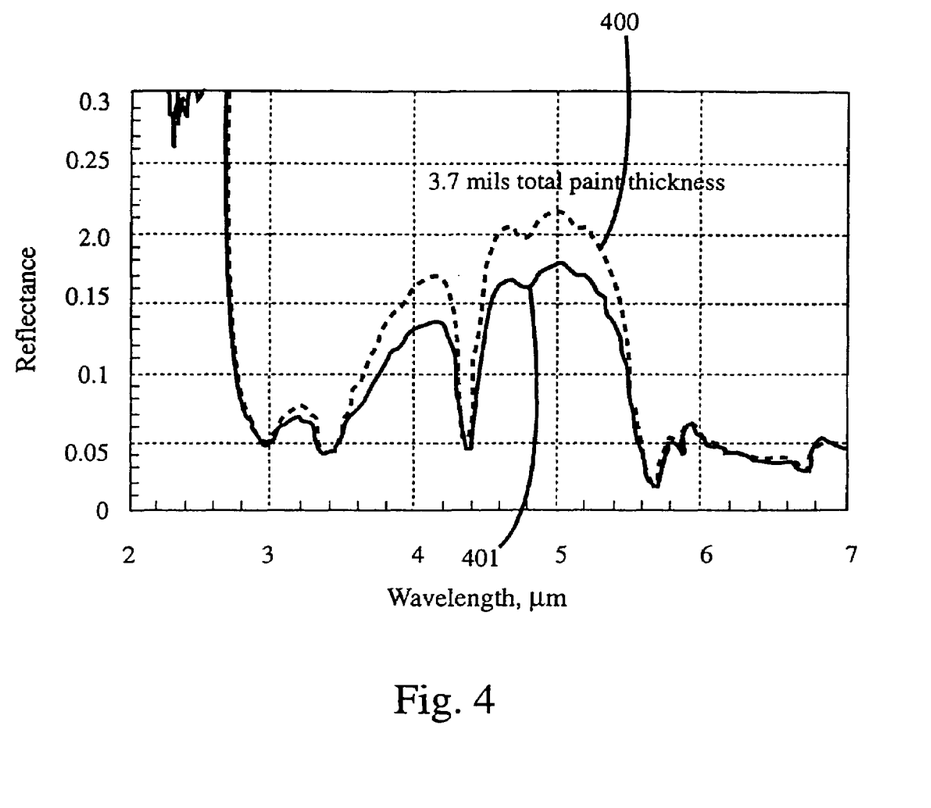
FIG. 4 illustrates the reflectivity principles behind the present invention in the form of a graph illustrating sample plots of reflectance versus wavelength for aluminum components.

FIG. 4 illustrates the reflectivity principles behind the present invention in the form of a graph illustrating sample plots of reflectance versus wavelength for aluminum components. The first plot 400 is for an uncorroded aluminum component with a layer of primer and paint having a total thickness of 0.0037" (3.7 mils). The second plot 401 is for a corroded aluminum component with the same layer of paint and primer. By comparing the plots 400 and 401 a difference will be seen between the two plots 400 and 401 in the area between approximately a wave length of 3.5 microns (higher reflectance) and a wave length of 5.5 microns, with a dip at approximately a wave length of 4.4 microns. The first plot 400 is stronger than the second plot 401 because the uncorroded aluminum reflects a higher portion of the infrared light passing through the paint than the corroded aluminum does.

The above describes a basic implementation of the present invention. The invention may take a variety of embodiments designed to provide additional features. For instance, dependent upon the coating used on the substrate or upon the particular structural features in which an operator has interest, it may be expedient to view the substrate in a variety of wavelengths. The system may therefore include a multiplicity of optical filters which may be manually or automatically changeable in order to accomplish this objective. Likewise, the polarity of the polarizers may be rotatable in order to provide imaging of the substrate in a variety of combinations of polarities. As an additional modification, the provision of imaging at a variety of wavelengths and/or combinations of polarities could be accomplished by means of a multiple imaging device. This would allow the system to create a plurality of images simultaneously for rapid processing. In this respect, the multiple imaging device could process and generate images at several different wavelengths and polarities.

Following the above line of additions, the system could include a computer for processing the images provided by the system in order to provide improved images of selected irregular structural features of the substrate. As will be recognized by those in the art, a given structural feature of the substrate will be more readily observable in certain wavelengths and/or combinations of polarities than in others. The computer could contain a database of information with respect to which combinations were effective for viewing, for instance, corrosion. The operator would then simply indicate to the computer that he desired to view corrosion, and the computer would automatically select the combination or combinations appropriate to so doing. Additionally, images or signal taken in the IR from the surface or internal to the coating may be substrated out as background signals to enhance images taken on the substrate to be inspected for an improved composite image of the substrate surface.

The computer could additionally be programmed to recognize selected structural features of the substrate. As will be apparent to those in the art, this can be accomplished by means of software operative to search for substrate patterns. Such substrate patterns may include specific corrosion characteristics, extrusions and inclusions of the surface and other characteristics which indicates that the substrate is damaged in some manner. Once identified, the features could be labeled for the user. For instance, the computer could provide color-coded images of the substrate. The color-coding could operate as a function of feature type or level of structural integrity. In the former case, the computer could assign, for instance, red to corrosion and black to cracking. In the later case, the computer could assign, for instance, red to undamaged portions of the substrate, yellow to moderately damaged portions of the substrate, and blue to seriously damaged portions of the substrate. In any event, the computer operates to perform a preliminary analysis which may be useful to the operator.

The system could incorporate an automatic feedback loop driven by hardware or software, operative to rapidly find the best combinations of wavelengths and/or polarities for viewing the substrate, or selected structural features of the substrate. The computer would experiment with various combinations and use the above mentioned identification techniques in order to determine which combinations were working most effectively. It could then rapidly determine which combination or combinations were most appropriate for the task at hand, and automatically employ those combinations.

Furthermore, the system could comprise an automatic pointer device operative to generate an alarm or automatic notification when selected structural features are observed. This could take the form of software operative to impose a crosshair on the image or software or hardware operative to automatically zoom on selected structural features of the image, for instance. The latter would be highly useful in applications where it is necessary to analyze large objects for potentially subtle signs of damage. The operator could move the view of the system over the object and, when the system detected a defect of below a preset visibility threshold, it would automatically zoom in on the defect in question to ensure identification of the defect.

In further keeping with the above line of improvements, a position sensor could be included in order to store coordinates on the substrate for future reference. The coordinates could be identified, for instance, with respect to a reference point on the substrate. In this example, the position sensor could record the coordinates of the system on the substrate as a function of distance to and direction from the reference point. Marking by the position sensor could be accomplished automatically by a computer, or could be performable by the operator.

Still a further embodiment of the invention would provide a communications device, such as a communications port or transmitter, operative to put the system in communication with an external device or network. Including a communications device could enhance the usefulness of the system in many ways. For instance, an external computer could contain a database of coatings available on the market. In order to inspect the substrate, the operator would first identify its coating and send a query to the external computer. The external computer could then provide the system with information as to which combination of wavelengths and/or polarities was appropriate in order to effectively view the substrate. A further improvement would use the system's own imaging system to automatically assess features of the coating and send values with respect to these features to the external computer. The external computer could compare these values to values in its own database and identify the coating itself before sending the relevant data. This would eliminate the need of the operator to identify the coating in question.

Another use of communications capability would be to allow an operator to call up remotely stored control images. The control images could be either images of an undamaged substrate of the same design or the same substrate at an earlier time. The control image could be displayed on the same screen as the image then being generated in order to allow convenient comparison by the operator. The generated image could additionally be compared to the control image by hardware or software operative to identify discrepancies, in order to further clarify which structural features of the substrate were irregular. This latter method would be particularly helpful in situations in which the substrate has, in its undamaged form, peculiar features which may otherwise appear to be damage. The computer could use the control image as a mask to eliminate all structural features expected to be in the substrate in order to ensure that physically irregular but appropriate features were not identified as damage.

It will additionally be apparent to those in the art that the images generated by use of the system and method of the present invention may be further operated upon in order to provide additional information. For instance, a database could be established for the purpose of storing images taken of a given substrate over time. The images so stored could be compared, for instance by a computer, in order to assess the rate at which damage was occurring to the substrate. The approximate time at which the substrate would become unsuitable for use could therefore be extrapolated, and projected repair and maintenance schedules developed.

Still a further embodiment of the invention would use the infrared light source to cause the substrate to emit light. This could be more easily accomplished if the infrared light source were a laser. Certain structural features of the substrate will have different chemical compositions than the undamaged portion of the substrate. They will therefore emit light of different wavelengths than the undamaged portion of the substrate. The system could therefore be configured to view, for instance, corrosion by means of selecting the selected wavelengths with respect to the wavelength of light emitted by corrosion on the substrate. A filtered IR light source (spectral/polarized) could also be used in the embodiment as just described.

Obviously, any of the above described features could be combined. For instance, the aforementioned damage-over-time analysis method described would be particularly useful in combination with a position sensor as described further above. Additionally, while the present invention has been described in connection with inspection of substrates for damage, it is understood that the invention may be employed in a variety of applications. For instance, the present invention could be used to read serial codes or other identifying marks on substrates.

Additional modifications and improvements of the present invention may also be apparent to those of ordinary skill in the art. Thus, the particular combination of elements described and illustrated herein is intended to represent only certain embodiments of the present invention, and is not intended to serve a limitation on systems and methods within the spirit and scope of the invention.

What is claimed is:

1. A system for imaging the surface of a substrate through a coating on the substrate, comprising:
   a) an infrared light source positioned to cast infrared light upon the substrate to thereby create reflected light;
   b) a focal plane array positioned to receive the reflected light off the substrate surface and generating an image therefrom; and
   c) at least one spectral optical filter disposed between the substrate and the focal plane array so as to pass only coating transparent wavelengths of the reflected light along an optical path between the infrared light source and the focal plane array thereby visually revealing structural features of the substrate as at least one image.

2. The system of claim 1, further comprising a multiplicity of optical filters disposed between the substrate and the focal plane array for generating images a plurality of selected wavelengths and for imaging structural features of the substrate.

3. The system of claim 1, further comprising a multiple imaging device in communication with the focal plane array for simultaneously imaging a plurality of structural features of the substrate.

4. The system of claim 1, further comprising a computer combining and enhancing images generated by the system to thereby generate collective images of selected structural features of the substrate.

5. The system of claim 1, further comprising a computer programmed with substrate patterns for color-coding selected structural features of the substrate within the image based on the substrate patterns so as to provide visual categorization of the structural features.

6. The system of claim 1, further comprising a position sensor for marking reference points on the surface of the substrate so as to store coordinates of structural features on the substrate.

7. The system of claim 1, further comprising a computer comparing images generated at selected wavelengths in a feedback loop so as to automatically enhance image quality of selected structural features of the substrate based upon preselected enhancement criteria.

8. The system of claim 1, where in the light source, the focal plane array and the at least one optical filters are collectively formed within a hand-held device transportable by a single human operator.

9. The system of claim 1, further comprising:
   a) a first polarizer disposed between the infrared light source and the substrate for polarizing the infrared light to a first selected polarity; and
   b) a second polarizer disposed between the substrate and the focal plane array for polarizing the reflected light to a second selected polarity.

10. The system of claim 9, wherein the first selected polarity and second selected polarity are oppositely configured so as to prevent reflected light corresponding to selected structural features of the substrate from being received upon the focal plane array.

11. The system of claim 9, further comprising a multiplicity of optical filters providing imaging at a plurality of selected wavelengths so as to form an image of a plurality of structure features from the substrate.

12. The system of claim 9, wherein the polarities of the first and second polarizers are rotatable so as to selectably provide a plurality of polarities for imaging structural features from the substrate.

13. The system of claim 9, further comprising a multiple imaging device in communication with the focal plane array for simultaneously imaging a plurality of structural features of the substrate.

14. The system of claim 9, further comprising a computer combining and enhancing images generated by the system to thereby generate collective images of selected structural features of the substrate.

15. The system of claim 9, further comprising a computer programmed with substrate patterns for color-coding selected structural features of the substrate within the image based on the substrate patterns so as to provide visual categorization of the irregular structure features.

16. The system of claim 9, further comprising a position sensor for making reference points on the surface of the substrate so as to store coordinates of structure features of the substrate.

17. The system of claim 9, further comprising a computer comparing images generated at a plurality of selected wavelengths and selected polarities in a feedback loop so as to automatically enhancing the image quality of selected structural features of the substrate based upon selected criteria.

18. The system of claim 9, wherein the infrared light source, the focal plane array and the at least one optical filter are collectively formed within a hand-held device transportable by a single human operator.

19. The system of claim 1, further comprising a communication device for transferring the revealed structure features to a remote human viewable medium.

20. The system of claim 1, further comprising a communication device for transferring the revealed structure features to a database.

21. The system of claim 1, further comprising a communication device for transferring the revealed structural features to a database.

22. A method of imaging the surface of a substrate through a coating on the substrate, comprising:
   a) directing infrared light upon the substrate;
   b) reflecting the infrared light from the substrate to thereby create reflected light;
   c) filtering to pass only coating transparent wavelengths of the reflected light;
   d) receiving the filtered reflected light on a focal plane array; and
   e) generating at least one image from the focal plane array so as to visually reveal structural features of the substrate.

23. The method of claim 22, further comprising comparing a plurality of images generated upon the focal plane array as a function of time to thereby establish a rate of degradation for the substrate.

24. The method of claim 22, further comprising selecting the coating transparent wavelengths from a database storing reflectivity characteristics of coatings found on substrate.

25. The method of claim 22, further comprising comparing the generated images with a pre-selected control image to thereby identify irregular structural features of the substrate.

26. The method of claim 22, further comprising:
   a) directing the infrared light through a first polarizer before the infrared light reaches the substrate so as to polarize the infrared light to a first selected polarity; and
   b) directing the reflected light through a second polarizer before the infrared light reaches the focal plane array so as to polarize the reflected to a second polarity.

27. The method of claim 26, wherein the first selected polarity and the second polarity are oppositely features of the substrate from being received upon the focal plane.

28. The method of claim 26, further comprising comparing a plurality of images generated upon the focal plane array as a function of time to thereby establish a rate of degradation for the substrate.

29. The method of claim 26, further comprising selecting the selected wavelengths and first and second selected polarities from a database storing reflectivity and characteristics of coatings found on substrates.

30. The method of claim 26, further comprising comparing the generated images with a pre-selected control image to thereby identify irregular structural features of the substrate.

31. The method of claim 22, further comprising transferring the generated images to a remote human viewable medium.

* * * * *

UNITED STATES PATENT AND TRADEMARK OFFICE
CERTIFICATE OF CORRECTION

PATENT NO. : 7,193,215 B2
APPLICATION NO. : 11/211304
DATED : March 20, 2007
INVENTOR(S) : Don DiMarzio, Robert Silberstein and John Weir It is certified that error appears in the above-identified patent and that said Letters Patent is hereby corrected as shown below:

Column 8
Line 61, please insert --in-- before "a"

Column 9
Line 38, please delete "structure" and insert --structural--
Line 55, please delete "structure" and insert --structural--
Line 57, please delete "making" and insert --marking--
Line 58, please delete "structure" and insert --structural--
Line 63, please delete "enhancing" and insert --enhance--

Column 10
Line 6, please delete "structure" and insert --structural--
Line 9, please delete "structure" and insert --structural--
Line 32, please insert --the-- before "substrate"
Line 34, please delete "images" and insert --image--
Line 44, please insert --light-- before "to a second" and insert --selected-- before "polarity"
Line 46, please insert --selected-- before "polarity"

Signed and Sealed this

Twenty-third Day of November, 2010

David J. Kappos
*Director of the United States Patent and Trademark Office*